(12) United States Patent
Hartley

(10) Patent No.: US 8,740,964 B2
(45) Date of Patent: *Jun. 3, 2014

(54) ENDOLUMINAL DELIVERY DEVICE

(75) Inventor: David Ernest Hartley, Wannanup (AU)

(73) Assignee: Cook Medical Technologies LLC, Bloomington, IN (US)

( * ) Notice: Subject to any disclaimer, the term of this patent is extended or adjusted under 35 U.S.C. 154(b) by 1602 days.

This patent is subject to a terminal disclaimer.

(21) Appl. No.: 11/654,422

(22) Filed: Jan. 17, 2007

(65) Prior Publication Data

US 2007/0185558 A1 Aug. 9, 2007

Related U.S. Application Data

(60) Provisional application No. 60/759,883, filed on Jan. 18, 2006.

(51) Int. Cl.
*A61F 2/95* (2013.01)

(52) U.S. Cl.
USPC ............................................. 623/1.12

(58) Field of Classification Search
USPC ................ 623/1.11–1.54; 606/108, 194, 200; 604/96.01–103.1, 525
See application file for complete search history.

(56) References Cited

U.S. PATENT DOCUMENTS

| 5,338,296 | A | * | 8/1994 | Dalessandro et al. | ... 604/103.05 |
|---|---|---|---|---|---|
| 5,456,665 | A | * | 10/1995 | Postell et al. | ............ 604/103.09 |
| 5,507,766 | A | * | 4/1996 | Kugo et al. | ................... 606/194 |
| 5,658,263 | A | * | 8/1997 | Dang et al. | ..................... 604/525 |
| 5,700,269 | A | * | 12/1997 | Pinchuk et al. | ............... 606/108 |
| 5,713,917 | A | | 2/1998 | Leonhardt et al. | |
| 5,728,063 | A | * | 3/1998 | Preissman et al. | ........ 604/103.09 |
| 6,206,852 | B1 | * | 3/2001 | Lee | ............. 604/96.01 |
| 6,287,329 | B1 | * | 9/2001 | Duerig et al. | ................ 623/1.11 |
| 6,497,678 | B2 | * | 12/2002 | Schock | ..................... 604/103.06 |
| 6,520,983 | B1 | * | 2/2003 | Colgan et al. | ................ 623/1.11 |
| 6,939,370 | B2 | * | 9/2005 | Hartley et al. | ................ 623/1.11 |
| 7,527,632 | B2 | * | 5/2009 | Houghton et al. | ............ 606/108 |
| 7,611,529 | B2 | * | 11/2009 | Greenberg et al. | .......... 623/1.11 |
| 2003/0212410 | A1 | | 11/2003 | Stenzel et al. | |
| 2004/0106974 | A1 | * | 6/2004 | Greenberg et al. | .......... 623/1.11 |
| 2004/0193177 | A1 | * | 9/2004 | Houghton et al. | ............ 606/108 |

FOREIGN PATENT DOCUMENTS

| WO | WO 99/43379 | 9/1999 |
|---|---|---|
| WO | WO 01/56505 | 8/2001 |
| WO | WO 2004/002371 | 1/2004 |

* cited by examiner

*Primary Examiner* — Kathleen Holwerda
(74) *Attorney, Agent, or Firm* — Richard J. Godlewski

(57) ABSTRACT

A highly flexible delivery device (2) for a stent graft (6) particularly for deployment into the thoracic arch of a patient. The delivery device has a distal handle (7), a pusher catheter (4) extending proximally from the handle to a proximal nose cone dilator (11), a guide wire catheter (3) extending from the proximal nose cone dilator to the pusher catheter. To give flexibility the guide wire catheter comprises a nitinol tube, the nose cone dilator has a high flexibility and the pusher catheter has a graded flexibility being more flexible at its proximal end than at its distal end. The graded flexibility can be provided by joined segments (4a, 4b and 4c) of different flexibility or by a inner metal tube (72) to give rigidity over some of the length. Alternatively the graded flexibility can be provided by tapering the wall thickness (80, 80a) of the pusher catheter.

20 Claims, 6 Drawing Sheets

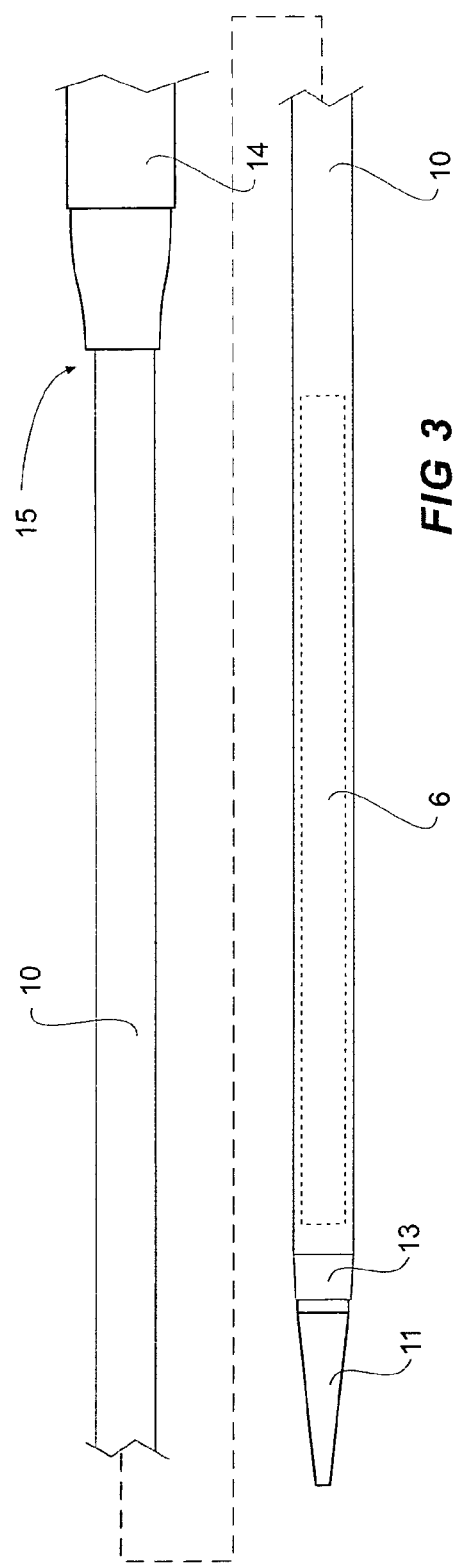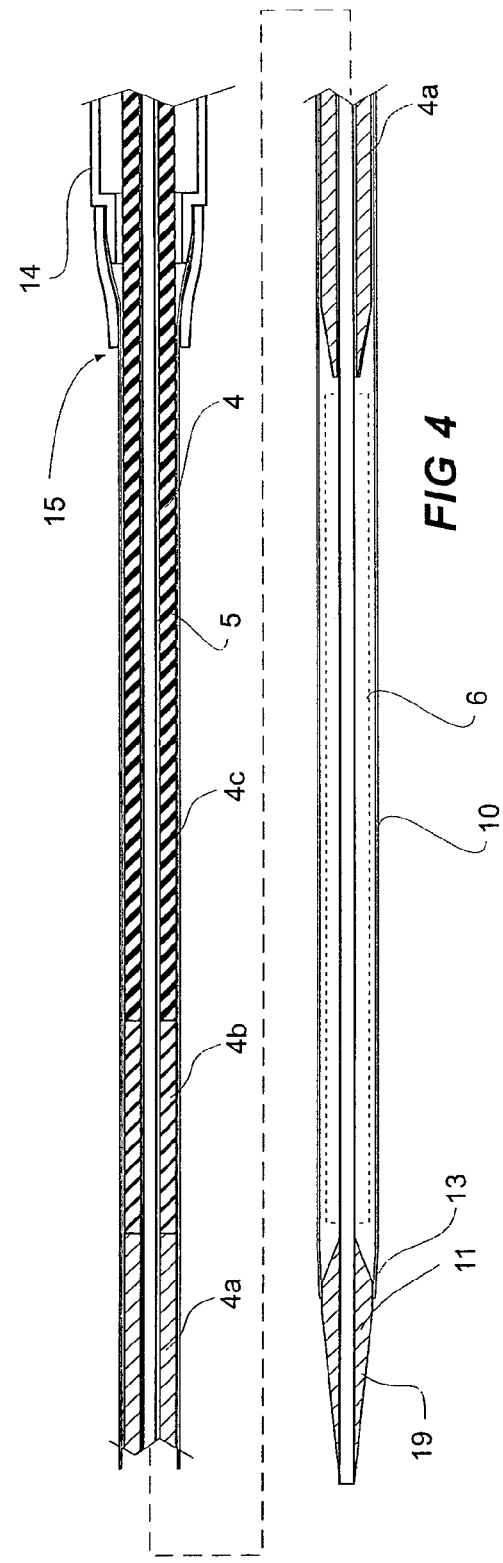

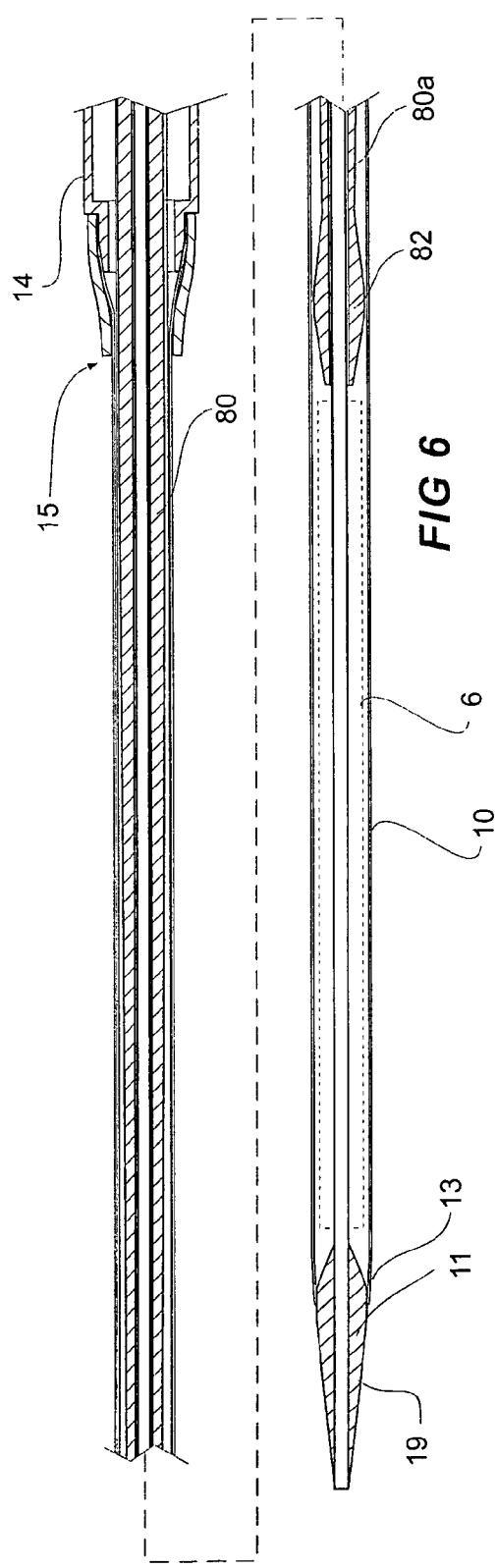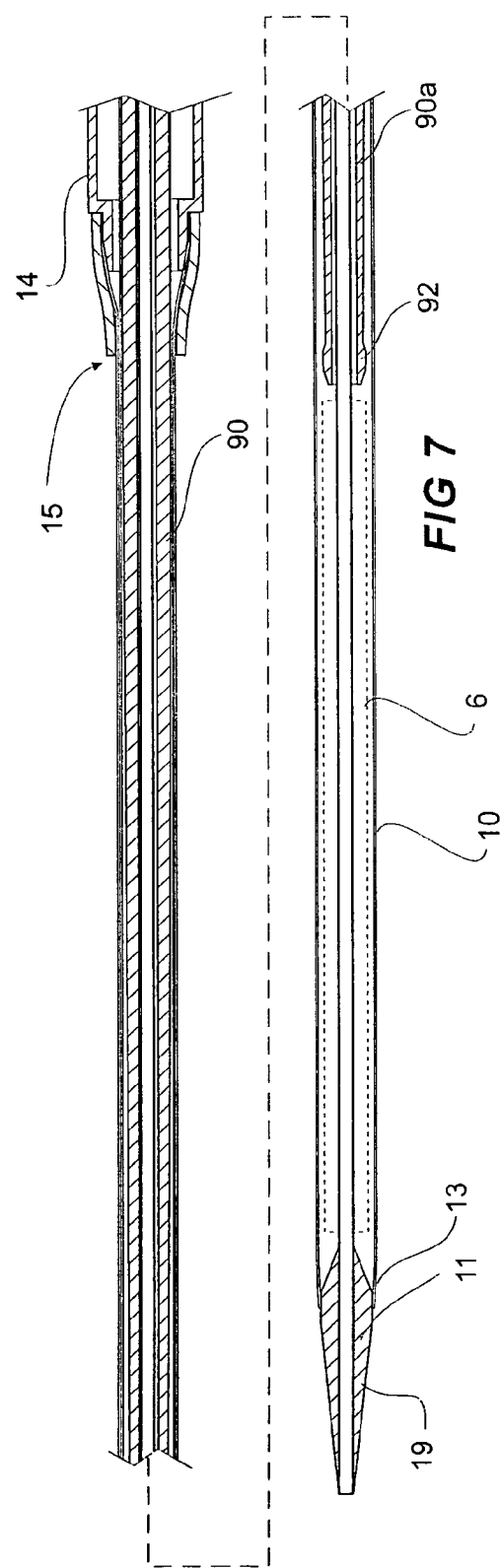

ENDOLUMINAL DELIVERY DEVICE

CROSS-REFERENCE TO RELATED APPLICATIONS

This application claims priority of provisional application Ser. No. 60/759,883, filed Jan. 18, 2006.

TECHNICAL FIELD

This invention relates to a delivery device or deployment device for intraluminal or endovascular delivery of a stent graft and particularly for delivery into the thoracic aorta.

BACKGROUND OF THE INVENTION

The invention will be discussed generally with respect to deployment of a stent graft into the thoracic aorta but is not so limited and may apply to deployment into other body lumens.

The thoracic arch has a significant curve which may be compounded, that is the curve may exist in more than one plane. This means that a delivery device, which in prior art devices has been relatively rigid, engages significantly against the walls of a vessel into which it is deployed and can cause unnecessary trauma and distortion of the vessel. If a stent graft is subsequently deployed into such a distorted vessel then when the delivery device is removed then the stent graft will be distorted when the vessel returns to its original configuration with undesirable results.

At the same time a degree of rigidity of a deployment device is desirable so that it can be pushed from outside the patient through a tortuous vasculature via the femoral artery, common iliac artery, aortic bifurcation, descending aorta and into the thoracic aorta and aortic arch.

The present invention proposes a delivery device which will assist with overcoming these opposing problems or at least provide a practitioner with a useful alternative.

Throughout this specification the term distal with respect to a portion of the aorta, a deployment device or a stent graft is intended to mean the portion of the aorta, deployment device or stent graft further away in the direction of blood flow away from the heart and the term proximal is intended to mean the portion of the aorta, deployment device or end of the stent graft nearer to the heart. When applied to other vessels similar terms such as caudal and cranial should be understood.

SUMMARY OF THE INVENTION

In one form the invention is said to reside in an endovascular delivery device and stent graft mounted thereon;
the delivery device comprising a distal handle,
a pusher catheter extending proximally from the handle,
a proximal nose cone dilator, and
a guide wire catheter extending from the proximal nose cone dilator to the pusher catheter,
wherein the guide wire catheter comprises a nitinol tube.

Preferably the nose cone dilator also has a high flexibility.

The pusher catheter can also have a graded flexibility being more flexible at its proximal end than at its distal end.

Preferably the pusher catheter comprises a longitudinal lumen therethrough and the guide wire catheter extends through the longitudinal lumen so that the guide wire catheter is movable longitudinally and rotationally with respect to the pusher catheter.

The nitinol guide wire catheter can have a diameter in the range of from 1.0 mm to 1.5 mm and a wall thickness of from 0.1 to 0.25 mm. More particularly the nitinol guide wire catheter can have a diameter of 1.28 mm and a wall thickness of 0.12 mm.

Preferably the nose cone dilator has a length of from 60 mm to 100 mm and a hardness of from 58 to 45 Shore D. More particularly the nose cone dilator has a length of 80 mm and a hardness of 48 Shore D and is preferably formed from a polyurethane.

The pusher catheter can comprise a first proximal portion with a higher flexibility and a second distal portion with a lower flexibility whereby the proximal portion can flex to assist in conformation with tortuosity of vessels into which the delivery device is deployed and the distal portion provides rigidity for progressing a delivery device through the vessels. The first portion can have a length of from 5 to 20 cms and a hardness of from 45 to 55 Shore D. More particularly the first portion can have a length of from 5 to 20 cms and a hardness of 48 Shore D. The second portion can have a hardness of from 50 to 60 Shore D. More particularly the second portion can have a hardness of 58 Shore D.

The first portion and the second portion are preferably formed from varying grades of polyurethane and the first portion and the second portion are preferably joined together by gluing or heat sealing.

There can also be an intermediate portion of pusher catheter between the first portion and the second portion comprising a flexibility between that of the first portion and the second portion. The intermediate portion of pusher catheter between the first portion and the second portion can have a length of from 5 to 20 cms and a hardness of from 48 to 55 Shore D.

There can be further provided a flexible sheath over the pusher catheter and extending distally to the nose cone dilator.

Preferably the nitinol guide wire catheter has flexibility which is in the range of 10 to 30 times greater than a corresponding stainless steel catheter and more particularly a flexibility 25 times more than a corresponding stainless steel catheter. Flexibility can be measured by hanging a weight on a cantilevered portion of catheter and measuring the deflection of the tip thereof.

In an alternative embodiment in the pusher catheter comprises a flexible polyurethane tube having a lumen therethrough and a metal cannula extending through the lumen from a distal end of the pusher catheter towards a proximal end of a pusher catheter whereby to make the distal end more rigid than the proximal end.

Alternatively the pusher catheter comprises a relatively thin walled flexible polyurethane tube having a lumen therethrough.

Alternatively the pusher catheter comprises a tapered wall flexible polyurethane tube having a lumen therethrough and having a reduced outer diameter towards the proximal end thereof.

Preferably the pusher catheter comprises a low friction coating on at least a distal portion thereof. The coating can comprise a PTFE tube on the pusher catheter.

This then generally describes the invention but to assist with understanding reference will now be made to various embodiments if the invention with the assistance of the accompanying drawings.

BRIEF DESCRIPTION OF THE DRAWING

FIG. 3 shows a side view of a portion of the deployment device of FIG. 1;

FIG. 4 shows a longitudinal cross sectional view of the embodiment shown in FIG. 3;

FIG. 6 shows a longitudinal cross sectional view of part of an alternative embodiment of a deployment device according to the present invention;

FIG. 7 shows a longitudinal cross sectional view of part of a further alternative embodiment of a deployment device according to the present invention.

DETAILED DESCRIPTION

Figure 1:
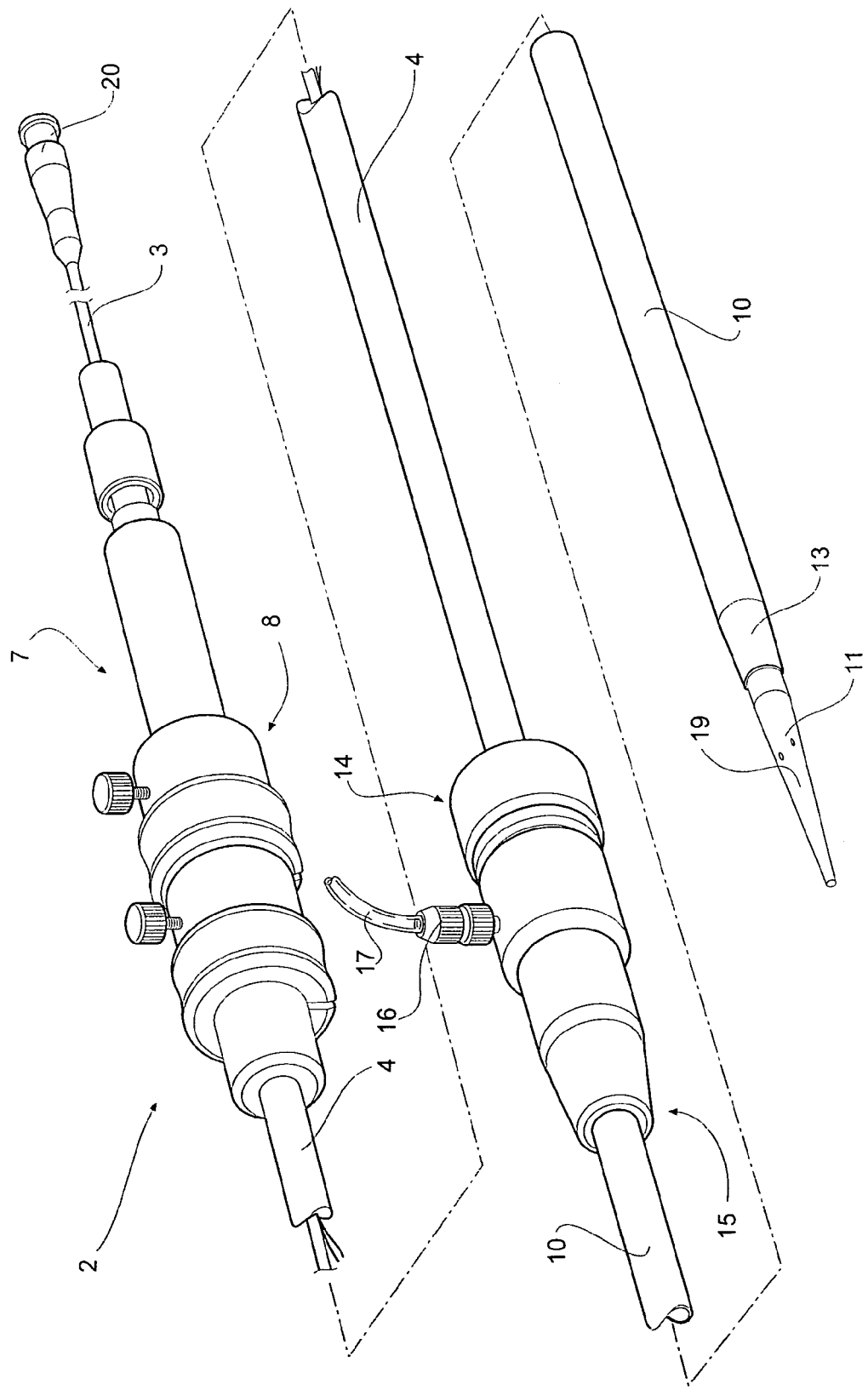
FIG. 1 depicts a introducer or delivery device according to one embodiment of the present invention.

FIGS. 1 to 4 depict a delivery device 2 incorporating highly flexible components according to one embodiment of the invention.

The delivery device 2 has a guide wire catheter 3 which extends from a handle 7 to a proximal tapered nose cone dilator 11 longitudinally through the passageway or lumen 5 (see FIG. 4) of a delivery catheter 4 which is connected to the handle 7 at its distal end. An introducer sheath 10 fits coaxially around the delivery catheter 4 and extends from a tapered proximal end 13 which includes a radiopaque marker to a connector valve and manipulator 14 attached about distal end 15 of the sheath. The introducer sheath 10 extends proximally to the nose cone dilator 11 and covers the stent graft 6 (shown dotted) during deployment and is withdrawn distally to expose the stent graft 6 during deployment when the deployment device is in a selected position within the vasculature of a patient. The stent graft or implantable device 6 (shown in dashed lines) is carried on the guide wire catheter 3 proximally of the delivery catheter 4 and distally of the nose cone dilator 11. Connector valve 14 includes a silicone disk (not shown) for preventing the backflow of fluids therethrough. The disk includes a slit for the insertion of the nose cone dilator 11 and delivery catheter 4. Connector 14 also includes side arm 16 to which polyvinyl tube 17 is connected for introducing and aspirating fluids therethrough. Nose cone dilator 11 includes tapered distal end 19 for accessing and dilating a vascular access site over a well-known and commercially available wire guide (not shown).

The wire guide is inserted in the vessel with an introducer needle using, for example, the well-known percutaneous vascular access Seldinger technique. A well-known male Luer lock connector hub 20 is attached at the distal end of the delivery catheter 4 for connection to syringes and other medical apparatus. The handle 7 at the distal end of the pusher catheter 4 remains outside a patient in use and carries the trigger wire release mechanisms 8 used to release the stent graft 6 retained on the delivery device by the use of trigger wires (not shown).

Figure 2:
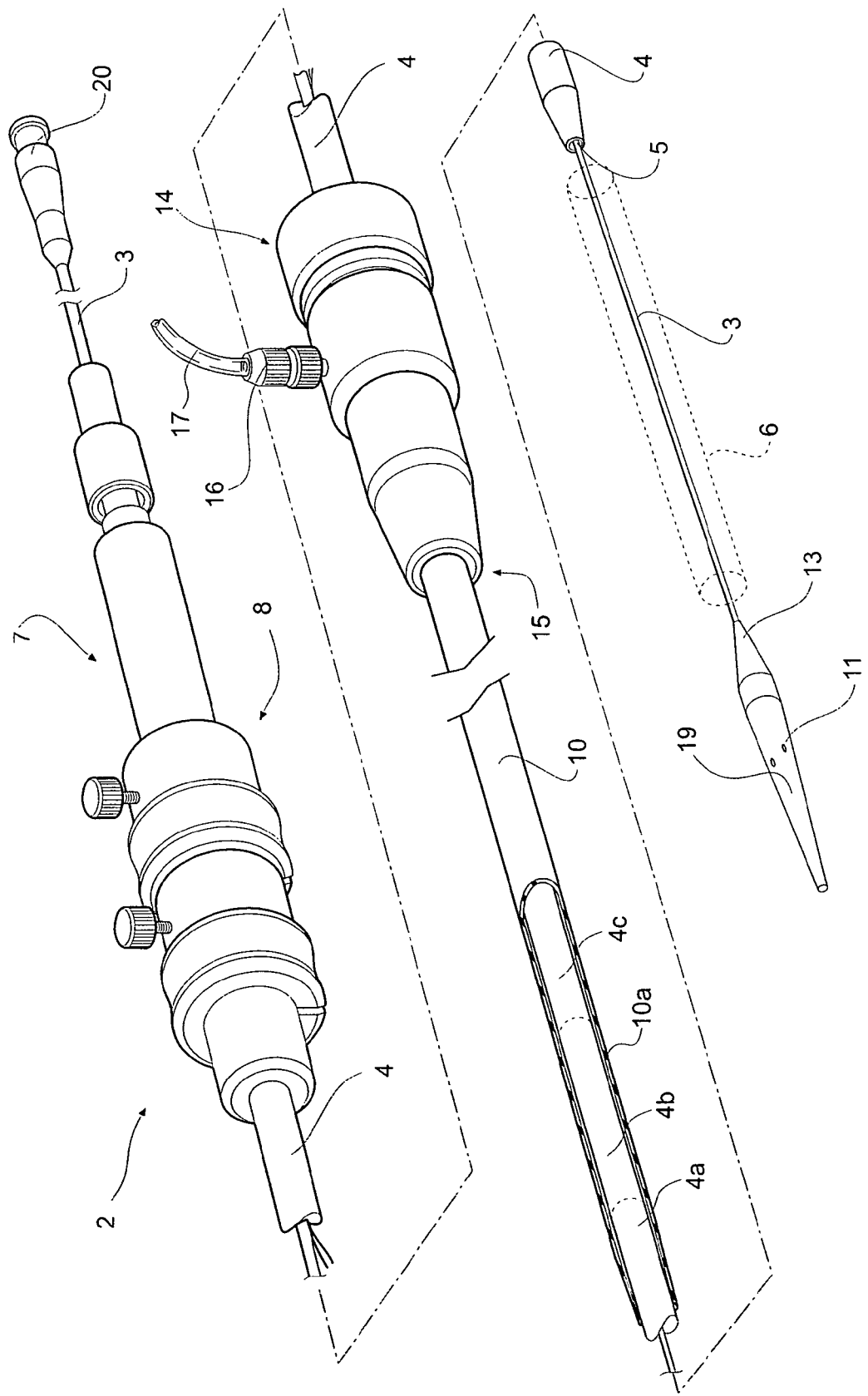
FIG. 2 depicts the introducer or delivery device of FIG. 1 with the sheath withdrawn and shown cutaway to show the components underneath it.

As can particularly be seen in FIG. 2 the sheath 10 has been retracted distally towards the handle 7 to expose the stent graft 6. The delivery catheter 4 can be seen in the cutaway portion 10a of the sheath 10 and is comprised of portions or segments of different flexibility. The most proximal portion 4a is made from a most flexible material, the portion 4b is made from a material which has slightly less flexibility and the portion 4c is least flexible. Although this embodiment is depicted with three zones of flexibility there may be only two zones of flexibility or there may be a continuous change on flexibility with the proximal end being most flexible and grading to less flexible.

The first portion 4a can have a length of from 5 to 20 cms and a hardness of from 45 to 55 Shore D. More particularly the first portion 4a can have a length of from 5 to 20 cms and a hardness of 48 Shore D. The intermediate portion 4b of pusher catheter between the first portion and the third portion can have a length of from 5 to 20 cms and a hardness of from 48 to 55 Shore D. The third portion 4c can have a hardness of from 50 to 60 Shore D. More particularly the third portion can have a hardness of 58 Shore D.

The nose cone dilator 11 is formed from a high flexibility material with substantially the same or greater flexibility than the portion 4a of the delivery catheter 4.

The nose cone dilator 11 can have a length of from 60 mm to 100 mm and a hardness of from 58 to 45 Shore D. More particularly the nose cone dilator has a length of 80 mm and a hardness of 48 Shore D and is preferably formed from a polyurethane.

The guide wire catheter 3 is formed from a tube of highly flexible nitinol so that it can easily bend to conform to the shape of vasculature into which it is deployed. Prior art guide wire catheters for delivery devices have been formed from stainless steel which while it has a degree of flexibility is more rigid than is desirable for curved parts of the vasculature such as the thoracic arch of a patient.

The nitinol guide wire catheter can have a flexibility which is in the range of 10 to 30 times greater than a corresponding stainless steel catheter and more particularly a flexibility 25 times more than a corresponding stainless steel catheter. Flexibility can be measured by hanging a weight on a cantilevered portion of catheter and measuring the deflection of the tip thereof.

FIG. 3 shows detail of the proximal end of the delivery device according to this embodiment of the invention. The sheath 10 extends from the connector valve and manipulator 14 which attached about distal end 15 of the sheath proximally to the nose cone dilator 11 and covers the stent graft 6 (shown dotted).

FIG. 4 shows the embodiment shown in FIG. 3 in longitudinal cross section. Within the sheath 10 the deployment catheter 4 is comprised of portions or segments of different flexibility. The most proximal portion 4a is made from a most flexible material, the portion 4b is made from a material which has slightly less flexibility and the portion 4c is least flexible.

In use when the delivery device is deployed into a patient via a femoral route and up to the thoracic arch for instance it is desirable that the proximal end of the delivery device is most flexible so that it can conform to the shape of the arch without providing unnecessary trauma to the wall of the aorta in that region. It is desirable too, that the more distal portion of the delivery device is more rigid. This ensures that the pushing force necessary to move the device through contorted vasculature from the incision on the femoral artery, through the iliac artery and aortic bifurcation into the descending aorta does not cause buckling of the more distal portion of the delivery device. The more proximal portion of the delivery device according to the present invention includes the nose cone dilator, the guide wire catheter and the more flexible proximal end of the delivery catheter.

Figure 5:
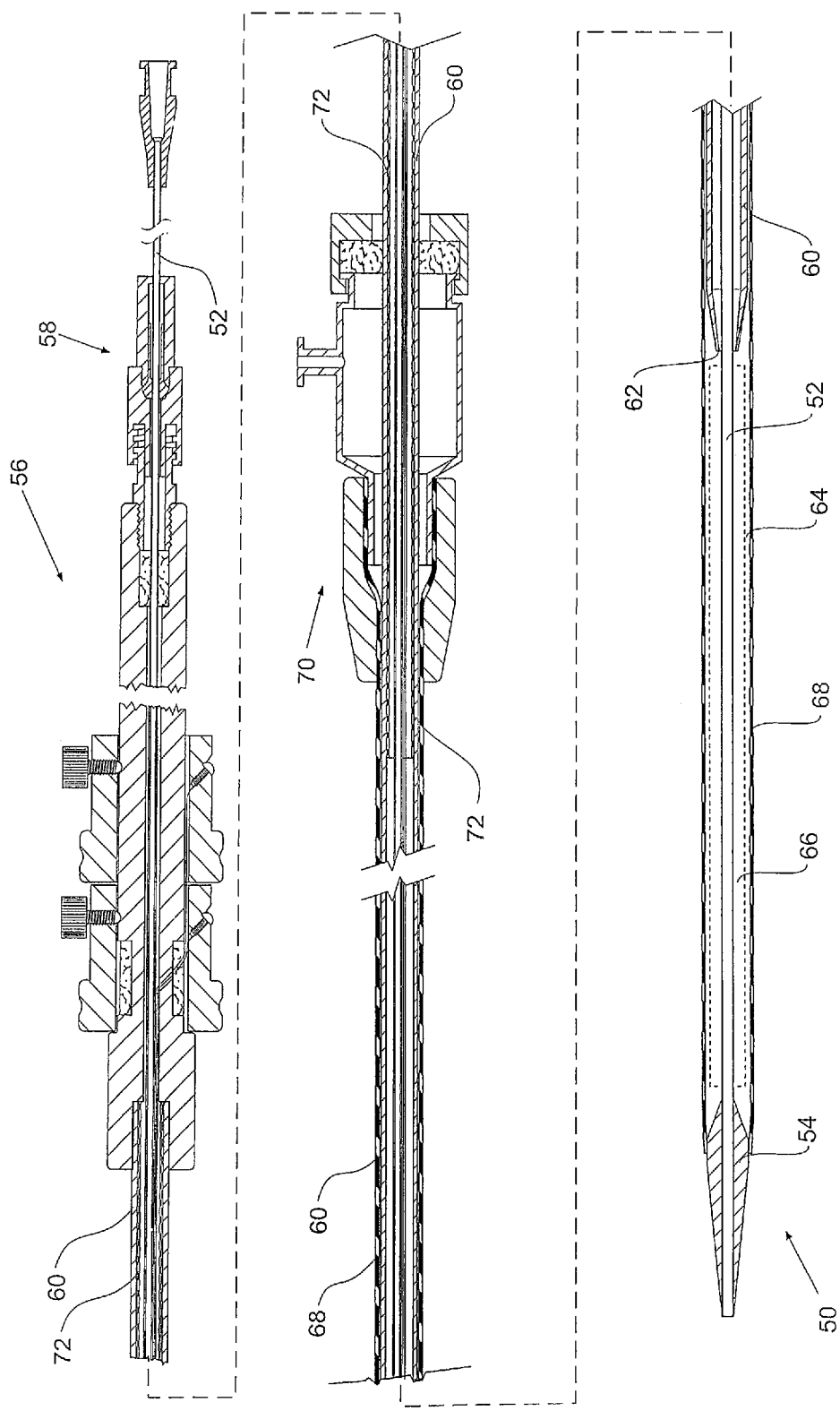
FIG. 5 shows a longitudinal cross sectional view of an alternative embodiment of a deployment device according to the present invention.

FIG. 5 shows a longitudinal cross sectional view of an alternative embodiment of a deployment device according to the present invention. In this embodiment the delivery device 50 comprises a guide wire catheter 52 extending from a proximal nose cone dilator 54 to a distal handle 56. A pin vice arrangement 58 locks the guide wire catheter into the handle 56 to prevent relative movement therebetween but when the pin vice 58 is released the guide wire catheter 52 can be moved longitudinally and rotationally with respect to the handle 56. A pusher catheter 60 extends distally from the handle 56. The proximal end 62 of the pusher catheter 60 terminates some distance distally of the nose cone dilator 54 to leave a region 64 into which a stent graft 66 (shown dotted) is received for deployment. A sheath 68 extends over the pusher catheter 60 from a sheath manipulator 70 to the nose cone dilator 54 to cover the stent graft 66 and to assist to hold the stent graft in a contracted condition for deployment. As discussed above it is useful to have a flexible proximal end to the deployment device to reduce the chance of trauma to the vasculature of a patient while at the same time to have a more rigid distal end to assist with introduction of the device. In this embodiment of the invention to provide more rigidity to the distal end of the pusher catheter 60 than the proximal end 62 there is provided a metal catheter 72 which is placed within the lumen of the pusher catheter to engage against the inside wall of the pusher catheter. The metal catheter 72 extends from the handle end of the pusher catheter to at least within the sleeve manipulator and valve 70 and preferably slightly proximal thereof. The metal catheter may extend to within 20 to 40 centimetres of the proximal end so that the final 20 to 40 centimetres of the proximal end of the pusher catheter is more flexible because it does not have the rigidifying effect of the metal catheter 72. The metal catheter 72 is particularly useful in the region of the pusher catheter traversed by the sheath manipulator 70 in use. The metal catheter 72 may be constructed for instance from stainless steel. By the use of the metal catheter of this embodiment the entire deployment catheter can be made from a more flexible material or may have a reduced wall thickness to give the desired greater flexibility particularly towards the proximal end of the pusher catheter.

In one embodiment the pusher catheter can have an outside diameter of 7 mm and a wall thickness of 1.5 mm and the stainless steel catheter inside the pusher catheter can have a diameter of 4 mm and a wall thickness of from 0.1 to 0.25 mm. Hence the stainless steel catheter is a firm push fit inside the pusher catheter.

FIG. 6 shows a longitudinal cross sectional view of part of an alternative embodiment of a deployment device according to the present invention. In this embodiment the deployment catheter 80 comprises a taper from the region of the sheath manipulator 14 to a narrowest point 80a just distal of the proximal end of the deployment catheter and then has an enlarged portion 82 at the proximal end. The enlarged portion 82 has a maximum diameter substantially the same as the non-tapered portion of the deployment catheter. The taper in the deployment catheter provides a change or variation in flexibility with increasing flexibility towards the proximal end thereof.

FIG. 7 shows a longitudinal cross sectional view of part of a further alternative embodiment of a deployment device according to the present invention. In this embodiment the deployment catheter 90 comprises a taper from the region of the sheath manipulator 14 to a narrowest point 90a just distal of the proximal end of the deployment catheter and then has a minor enlargement portion 92 at the proximal end. The taper in the deployment catheter provides a change or variation in flexibility with increasing flexibility towards the proximal end thereof.

Figure 8:
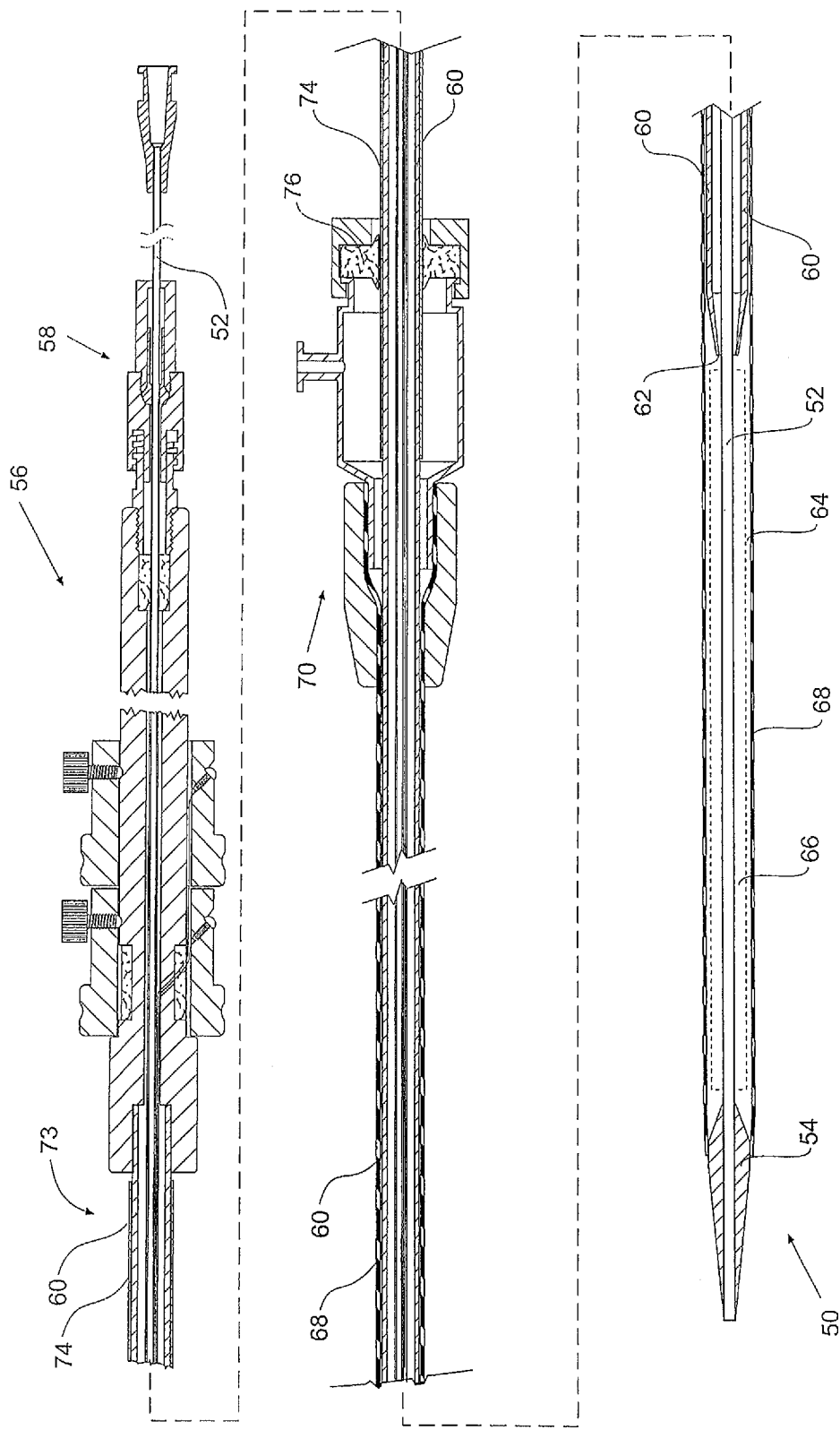
FIG. 8 shows a longitudinal cross sectional view of a still further alternative embodiment of a deployment device according to the present invention.

FIG. 8 shows a longitudinal cross sectional view of a still further alternative embodiment of a deployment device according to the present invention. This embodiment is substantially similar to that shown in FIG. 5 and the same reference numerals are used for corresponding items.

In this embodiment the delivery device 50 comprises a guide wire catheter 52 extending from a proximal nose cone dilator 54 to a distal handle 56. A pin vice arrangement 58 locks the guide wire catheter into the handle 56 to prevent relative movement therebetween but when the pin vice 58 is released the guide wire catheter 52 can be moved longitudinally and rotationally with respect to the handle 56. A pusher catheter 60 extends distally from the handle 56. The pusher catheter has a relatively thin wall to provide good flexibility to the catheter. The proximal end 62 of the pusher catheter 60 terminates some distance distally of the nose cone dilator 54 to leave a region 64 into which a stent graft 66 (shown dotted) is received for deployment. A sheath 68 extends over the pusher catheter 60 from a sheath manipulator 70 to the nose cone dilator 54 to cover the stent graft 66 and to assist to hold the stent graft in a contracted condition for deployment.

One reason for requiring less flexibility at the distal end of the pusher catheter is so that the load on the pusher catheter due to the silicone valve pieces 76 of the sheath manipulator and haemostatic valve 70. To reduce the load and thereby to reduce the requirement for less flexibility the distal end 73 of the pusher catheter 60 has a low friction coating on it such as a PTFE layer 74 around it. The PTFE coating 74 extends along the pusher catheter 60 at least from within the sheath manipulator and haemostatic valve 70 to just proximal of the handle 56. The low friction coating on it such as a PTFE layer 74 can be provided by a thin walled tube on the pusher catheter such as by heat shrinking onto the catheter of by any other suitable method. In one embodiment the pusher catheter can have an outside diameter of 7 mm and a wall thickness of 1.5 mm Throughout this specification various indications have been given as to the scope of this invention but the invention is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

What is claimed is:

1. An endovascular delivery device comprising a distal handle, a pusher catheter extending proximally from the handle; the pusher catheter comprising a distal end at the handle and a proximal end remote from the handle, the pusher catheter comprising a longitudinal lumen therethrough, a proximal nose cone dilator, a guide wire catheter extending from the proximal nose cone dilator to the handle, the guide wire catheter extending through the longitudinal lumen of the pusher catheter whereby that the guide wire catheter is movable longitudinally and rotationally with respect to the pusher catheter, a flexible sheath over the pusher catheter, the flexible sheath extending from a connector valve and manipulator on the pusher catheter proximally to the nose cone dilator, the flexible sheath and connector valve and manipulator being able to be withdrawn to expose a stent graft mounted onto the delivery device during deployment when the delivery device is in a selected position within the vasculature of a patient, the pusher catheter further comprising a taper whereby the pusher catheter reduces in diameter continuously along the length of the pusher catheter from the connector valve and manipulator proximally to a narrowest point just distal of the proximal end of the pusher catheter and an enlarged portion of the pusher catheter at the proximal end of the pusher catheter.

2. An endovascular delivery device as in claim 1 wherein the nose cone dilator has a high flexibility.

3. An endovascular delivery device as in claim 1 wherein the pusher catheter has a graded flexibility being more flexible at its proximal end than at its distal end.

4. An endovascular delivery device as in claim 1 wherein the guide wire catheter comprises nitinol and has a diameter in the range of from 1.0 mm to 1.5 mm and a wall thickness of from 0.1 to 0.25 mm.

5. An endovascular delivery device as in claim 4 wherein the nitinol guide wire catheter has a diameter of 1.28 mm and a wall thickness of 0.12 mm.

6. An endovascular delivery device as in claim 1 wherein the nose cone dilator has a length of from 60 mm to 100 mm and a hardness of from 58 to 45 Shore D.

7. An endovascular delivery device as in claim 1 wherein the nose cone dilator has a length of from 80 mm to 100 mm and a hardness of 48 Shore D.

8. An endovascular delivery device as in claim 1 wherein the nose cone dilator is formed from a polyurethane.

9. An endovascular delivery device as in claim 1 wherein the pusher catheter comprises at least a first proximal portion with a higher flexibility and a second distal portion with a lower flexibility whereby the proximal portion can flex to assist in conformation with tortuosity of vessels into which the delivery device is deployed and the distal portion provides rigidity for progressing a delivery device through the vessels.

10. An endovascular delivery device as in claim 9 wherein the first proximal portion has a length of from 5 to 20 cms and has a hardness of from 45 to 55 Shore D.

11. An endovascular delivery device as in claim 9 wherein the first proximal portion has a length of from 5 to 20 cms and has a hardness of 48 Shore D.

12. An endovascular delivery device as in claim 9 wherein the second distal portion has a hardness of from 50 to 60 Shore D.

13. An endovascular delivery device as in claim 9 wherein the second distal portion has a hardness of 58 Shore D.

14. An endovascular delivery device as in claim 9 wherein the first proximal portion and the second distal portion are formed from varying grades of polyurethane.

15. An endovascular delivery device as in claim 9 wherein the first proximal portion and the second distal portion are joined together by gluing or heat sealing.

16. An endovascular delivery device as in claim 15 further comprising an intermediate portion of pusher catheter between the first proximal portion and the second distal portion comprising a flexibility between that of the first proximal portion and the second distal portion.

17. An endovascular delivery device as in claim 16 wherein the intermediate portion of the pusher catheter between the first proximal portion and the second distal portion has a length of from 5 to 20 cms and has a hardness of from 48 to 55 Shore D.

18. An endovascular delivery device-as in claim 1 wherein the pusher catheter comprises a flexible polyurethane tube having a lumen therethrough and a metal cannula extending through the lumen from a distal end of the pusher catheter towards a proximal end of the pusher catheter whereby to make the distal end more rigid than the proximal end.

19. An endovascular delivery device as in claim 1 wherein the pusher catheter comprises a thin walled flexible polyurethane tube having the longitudinal lumen therethrough.

20. An endovascular delivery device as in claim 1 wherein the pusher catheter comprises a low friction coating on at least a distal portion thereof.

* * * * *